United States Patent
Nelson et al.

(10) Patent No.: US 9,964,416 B2
(45) Date of Patent: May 8, 2018

(54) METHODS AND SYSTEMS FOR LOCATING HEALTH FACILITIES BASED ON COST OF HEALTHCARE

(75) Inventors: Edward Clark Nelson, Ann Arbor, MI (US); Gary Steven Strumolo, Beverly Hills, MI (US); Mark Schunder, Dearborn, MI (US)

(73) Assignee: Ford Global Technologies, LLC, Dearborn, MI (US)

(*) Notice: Subject to any disclaimer, the term of this patent is extended or adjusted under 35 U.S.C. 154(b) by 2074 days.

(21) Appl. No.: 13/021,309

(22) Filed: Feb. 4, 2011

(65) Prior Publication Data
US 2012/0203454 A1   Aug. 9, 2012

(51) Int. Cl.
*G01C 21/36* (2006.01)
*G06F 19/00* (2011.01)
*G06Q 30/02* (2012.01)

(52) U.S. Cl.
CPC ....... *G01C 21/3679* (2013.01); *G06F 19/327* (2013.01); *G06F 19/328* (2013.01); *G06Q 30/02* (2013.01)

(58) Field of Classification Search
CPC ...... G01C 21/00; G06Q 99/00; H04L 12/803; H04W 24/08; H04W 28/02; H04W 28/08
USPC ... 701/201, 202, 209, 211, 213, 214, 23, 25; 340/995.19, 988; 342/357.01, 357.06, 342/357.08, 357.13
See application file for complete search history.

(56) References Cited

U.S. PATENT DOCUMENTS

| | | | |
|---|---|---|---|
| 3,974,350 A | 8/1976 | Breed | |
| 5,365,516 A | 11/1994 | Jandrell | |
| 5,410,739 A | 4/1995 | Hart | |
| 5,465,079 A | 11/1995 | Bouchard et al. | |
| 5,653,462 A | 8/1997 | Breed et al. | |
| 5,686,910 A | 11/1997 | Timm et al. | |
| 5,748,473 A | 5/1998 | Breed et al. | |
| 5,829,782 A | 11/1998 | Breed et al. | |
| 5,845,255 A | 12/1998 | Mayaud | |
| 5,848,802 A | 12/1998 | Breed et al. | |
| 5,901,978 A | 5/1999 | Breed et al. | |
| 6,078,853 A | 6/2000 | Ebner et al. | |
| 6,104,296 A | 8/2000 | Yasushi et al. | |
| 6,128,482 A | 10/2000 | Nixon et al. | |
| 6,272,411 B1 | 8/2001 | Corrado et al. | |

(Continued)

OTHER PUBLICATIONS

Ford Motor Company, "SYNC with Navigation System," Owner's Guide Supplement, SYNC System Version 1 (Jul. 2007).

(Continued)

*Primary Examiner* — Genna M Mott
*Assistant Examiner* — Charles J Han
(74) *Attorney, Agent, or Firm* — Jennifer Stec; Brooks Kushman P.C.

(57) ABSTRACT

Various embodiments may include methods and systems for locating health facilities based on a cost of healthcare. Information may be received identifying a source for receiving health service cost information. Further, vehicle user insurance information may be transmitted to obtain health service cost information. The health service cost information may be received from the identified source and presented at a vehicle computer. The identified source may include information by or from a health facilities and/or information from one or more members of the public.

22 Claims, 8 Drawing Sheets

(56) References Cited

U.S. PATENT DOCUMENTS

| | | |
|---|---|---|
| 6,282,475 B1 | 8/2001 | Washington |
| 6,330,499 B1 | 12/2001 | Chou et al. |
| 6,353,785 B1 | 3/2002 | Shuman et al. |
| 6,445,300 B1 | 9/2002 | Luman |
| 6,474,683 B1 | 11/2002 | Breed et al. |
| 6,602,191 B2 | 8/2003 | Quy |
| 6,603,999 B2 | 8/2003 | Servaas |
| 6,734,799 B2 | 5/2004 | Munch |
| 6,762,684 B1 | 7/2004 | Camhi |
| 6,778,672 B2 | 8/2004 | Breed et al. |
| 6,793,242 B2 | 9/2004 | Breed et al. |
| 6,942,248 B2 | 9/2005 | Breed et al. |
| 6,944,536 B2 * | 9/2005 | Singleton ............. 701/410 |
| 6,946,966 B2 | 9/2005 | Koenig |
| 7,019,650 B2 | 3/2006 | Volpi et al. |
| 7,027,621 B1 | 4/2006 | Prokoski |
| 7,042,345 B2 | 5/2006 | Ellis |
| 7,050,897 B2 | 5/2006 | Breed et al. |
| 7,164,117 B2 | 1/2007 | Breed et al. |
| 7,266,430 B2 | 9/2007 | Basson et al. |
| 7,301,464 B2 | 11/2007 | Coulter |
| 7,534,206 B1 | 5/2009 | Lovitt et al. |
| 7,670,288 B2 | 3/2010 | Sher |
| 7,680,690 B1 | 3/2010 | Catalano |
| 7,693,625 B2 | 4/2010 | Bauerle et al. |
| 7,775,453 B2 | 8/2010 | Hara |
| 7,792,701 B2 | 9/2010 | Basson et al. |
| 7,805,224 B2 | 9/2010 | Basson et al. |
| 8,078,334 B2 | 12/2011 | Goodrich |
| 8,104,814 B2 | 1/2012 | Sartin et al. |
| 8,140,358 B1 | 3/2012 | Ling et al. |
| 8,149,111 B2 | 4/2012 | Monroe |
| 8,196,694 B2 | 6/2012 | Biondo et al. |
| 8,229,758 B2 | 7/2012 | Moncrease |
| 8,350,722 B2 | 1/2013 | Tewari et al. |
| 2001/0020902 A1 | 9/2001 | Tamura |
| 2001/0034617 A1 | 10/2001 | Kimata |
| 2002/0013788 A1 | 1/2002 | Pennell et al. |
| 2002/0099424 A1 | 7/2002 | Ferek-Petric |
| 2002/0118112 A1 | 8/2002 | Lang |
| 2002/0123833 A1 | 9/2002 | Sakurai et al. |
| 2003/0028792 A1 | 2/2003 | Plow et al. |
| 2003/0043045 A1 | 3/2003 | Yasushi et al. |
| 2003/0064748 A1 | 4/2003 | Stulberger et al. |
| 2003/0065432 A1 | 4/2003 | Shuman et al. |
| 2003/0208409 A1 | 11/2003 | Mault |
| 2004/0046666 A1 | 3/2004 | Yasuchi |
| 2004/0133082 A1 | 7/2004 | Abraham-Fuchs et al. |
| 2005/0125258 A1 | 6/2005 | Yellin et al. |
| 2005/0171660 A1 | 8/2005 | Woolford et al. |
| 2005/0190062 A1 | 9/2005 | Sullivan et al. |
| 2005/0192830 A1 | 9/2005 | Pugh et al. |
| 2006/0008058 A1 | 1/2006 | Dai et al. |
| 2006/0015254 A1 | 1/2006 | Smith |
| 2006/0022834 A1 | 2/2006 | Rosenfeld et al. |
| 2006/0059013 A1 | 3/2006 | Lowe |
| 2006/0161456 A1 | 7/2006 | Baker et al. |
| 2006/0271394 A1 | 11/2006 | Kelly |
| 2006/0290516 A1 | 12/2006 | Muehlsteff et al. |
| 2007/0088624 A1 | 4/2007 | Vaughn et al. |
| 2007/0233384 A1 | 10/2007 | Lee |
| 2008/0033644 A1 | 2/2008 | Bannon |
| 2008/0097552 A1 | 4/2008 | Dicks et al. |
| 2008/0097917 A1 | 4/2008 | Dicks et al. |
| 2008/0218376 A1 | 9/2008 | Dicks et al. |
| 2008/0249386 A1 | 10/2008 | Besterman et al. |
| 2008/0297336 A1 | 12/2008 | Lee |
| 2009/0070148 A1 | 3/2009 | Skocic |
| 2009/0292555 A1 | 11/2009 | Brown |
| 2010/0268051 A1 | 10/2010 | Prasad et al. |
| 2011/0193707 A1 | 8/2011 | Ngo |
| 2011/0210867 A1 | 9/2011 | Benedikt |
| 2011/0218839 A1 | 9/2011 | Shamaiengar |
| 2012/0112915 A1 | 5/2012 | Strumolo |
| 2012/0166680 A1 | 6/2012 | Masoud et al. |
| 2012/0171982 A1 | 7/2012 | Schunder et al. |
| 2012/0173336 A1 | 7/2012 | Strumolo |
| 2012/0182143 A1 | 7/2012 | Gaines et al. |
| 2012/0184237 A1 | 7/2012 | Gaines et al. |
| 2012/0185265 A1 | 7/2012 | Kochhar |

OTHER PUBLICATIONS

Ford Motor Company, "SYNC," Owner's Guide Supplement, SYNC System Version 1 (Nov. 2007).

Ford Motor Company, "SYNC with Navigation System," Owner's Guide Supplement, SYNC System Version 2 (Oct. 2008).

Ford Motor Company, "SYNC," Owner's Guide Supplement, SYNC System Version 2 (Oct. 2008).

Ford Motor Company, "SYNC with Navigation System," Owner's Guide Supplement, SYNC System Version 3 (Jul. 2009).

Ford Motor Company, "SYNC," Owner's Guide Supplement, SYNC System Version 3 (Aug. 2009).

Kermit Whitfield, "A hitchhiker's guide to the telematics ecosystem", Automotive Design & Production, Oct. 2003, http://findarticles.com, pp. 1-3.

Medical Procedures/Surgical Procedures What's the Cost?, 1st Health Insurance Quotes,com, printed Oct. 30, 2010.

Google Health, About Google Health, www.healthvault.com, Dec. 20, 2010.

Welcome to Microsoft Healthvault, Heath Vault, www.google.com/health, Dec. 20, 2010.

WebMD, www.webmd.com, Dec. 20, 2010.

* cited by examiner

METHODS AND SYSTEMS FOR LOCATING HEALTH FACILITIES BASED ON COST OF HEALTHCARE

TECHNICAL FIELD

Various embodiments relate to searching, locating, and presenting health facilities in a vehicle based on the vehicle's location. In some embodiments, the health facilities may be located based on a cost to a vehicle user for the healthcare.

BACKGROUND

Tools for providing health facility information to a vehicle occupant, including facilities that exist along a travel route, are known.

For example, U.S. Pat. No. 6,944,536 to Singleton discloses a method and system for identifying medical facilities along a travel route. The system includes an input device, a processor, a server database and a memory storing various information regarding medical facilities. For on-demand determination of medical facilities along a travel route, the input device includes a GPS receiver providing the current geographical coordinates of a patient requiring medical assistance to the processor. The processor compares the geographical coordinates of the patient to coordinates of medical facilities in the database to determine medical facilities near the patient. A user of the system may also input a type of medical emergency, preferred language and insurance information to refine the search for medical facilities. The processor may also calculate a projected travel route using navigational software. The identified medical facilities may be displayed to a user in any manner and/or saved in a navigational computer for reference in case of a medical emergency.

SUMMARY

One aspect includes a computer-implemented method for providing health care facility information in a vehicle. The method may include receiving at one or more computers a geographic location of a vehicle. Additionally, the method may include identifying at the one or more computers one or more health facilities based on the geographic location of the vehicle. Further, the method may include receiving at the one or more computers health condition information for a vehicle user and health care insurance information for the vehicle user.

Based on the vehicle user's health condition and health care insurance information, a health care service cost for the vehicle user at the one or more identified health care facilities may be determined at the one or more computers. Further, the health care service cost may be presented within a vehicle. The health care service cost may be presented audibly, visually, or both.

In another aspect, a system for providing health care facility information in a vehicle may include at least one computer configured to receive information from one or more members of the public. This information may include health care service costs and health care insurance information for the one or more members of the public.

The system may also include at least one vehicle computer housed in a vehicle communicating with the at least one computer. This vehicle computer may be configured to receive health care insurance information for a vehicle user and a health care service cost from the at least one computer based on the information from the one or more members of the public. The information from the at least one computer may be applicable to the vehicle user based on the health care insurance information for the vehicle user and the health care insurance information for the one or more members of the public. The vehicle computer may be further configured to present the health care service cost.

In some embodiments, the at least one vehicle computer may be further configured to determine if the information from the one or more members of the public is applicable to the vehicle user based on a service type for the vehicle user and a service type for the one or more members of the public.

In another aspect, a system includes at least one computer configured to receive information identifying a source for receiving health service cost information. The at least one computer may be further configured to transmit vehicle user insurance information to obtain health service cost information. Further, the at least one computer may be configured to receive the health service cost information from the identified source. The health service cost information may be at a vehicle computer.

These and other aspects will be better understood in view of the attached drawings and following detailed description of the invention.

BRIEF DESCRIPTION OF THE DRAWINGS

The figures identified below are illustrative of some embodiments of the invention. The figures are not intended to be limiting of the invention recited in the appended claims. The embodiments, both as to their organization and manner of operation, together with further object and advantages thereof, may best be understood with reference to the following description, taken in connection with the accompanying drawings, in which:

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

When a vehicle occupant is in need of medical assistance during a journey, locating a medical facility may be, in some cases, a critical decision. The decision becomes difficult when the vehicle user (e.g., driver and/or passenger) is out of state or in unfamiliar territory. For those who have health insurance, some of this difficulty is minimized because some insurance companies offer a "preferred provider option" (PPO) network. This permits an insured to use a nationwide network of healthcare professionals without incurring significant (or any) insurance costs. However, since this option is expensive, some individuals may opt for less expensive alternatives, but which provide less benefits. For example, these plans may have a very limited network of health facilities under contract and/or offer a limited amount of health care that is covered under the plan. In any case, whether or not an individual has health insurance and, if so, regardless of the type of plan, when travelling, such individuals may not be prepared with the costs for a health service prior to the visit, particularly if the health care is an emergency.

Detailed embodiments of the invention are disclosed herein. However, it is to be understood that the disclosed embodiments are merely exemplary of an invention that may be embodied in various and alternative forms. Therefore, specific functional details disclosed herein are not to be interpreted as limiting, but merely as a representative basis for the claims and/or as a representative basis for teaching one skilled in the art to variously employ the present invention.

It will be appreciated that the disclosure and arrangement of the figures is non-limiting. Accordingly, the disclosure and arrangement may be modified or re-arranged to best fit a particular implementation of the various embodiments of the invention.

Figure 1:
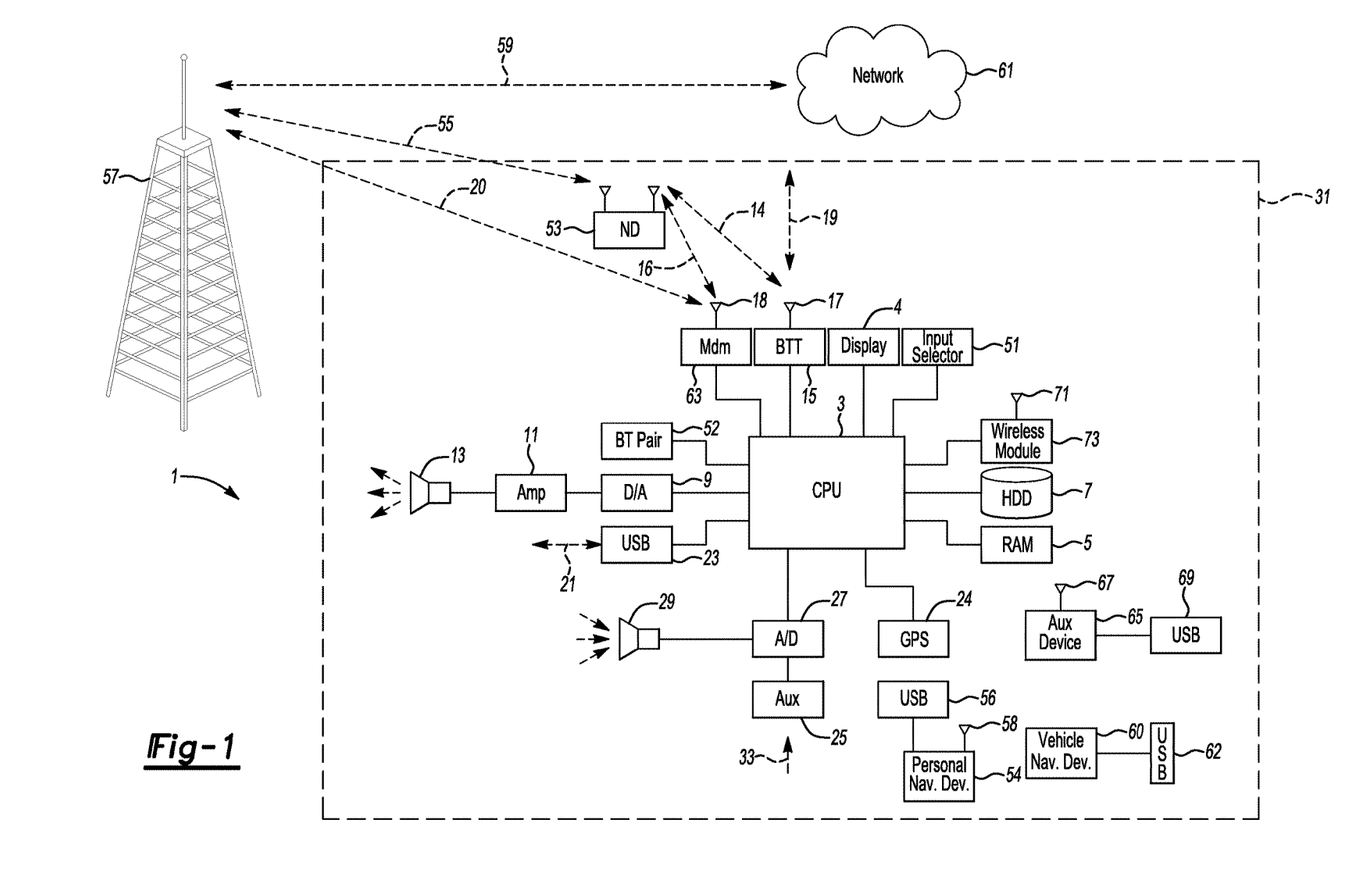
FIG. 1 is a block diagram of a vehicle computing system.

FIG. 1 illustrates an example block topology for a vehicle based computing system 1 (VCS) for a vehicle 31. An example of such a vehicle-based computing system 1 is the SYNC system manufactured by THE FORD MOTOR COMPANY. A vehicle enabled with a vehicle-based computing system may contain a visual front end interface 4 located in the vehicle. The user may also be able to interact with the interface if it is provided, for example, with a touch sensitive screen. In another illustrative embodiment, the interaction occurs through, button presses, audible speech and speech synthesis.

In the illustrative embodiment 1 shown in FIG. 1, a processor 3 controls at least some portion of the operation of the vehicle-based computing system. Provided within the vehicle, the processor allows onboard processing of commands and routines. Further, the processor is connected to both non-persistent 5 and persistent storage 7. In this illustrative embodiment, the non-persistent storage is random access memory (RAM) and the persistent storage is a hard disk drive (HDD) or flash memory.

The processor is also provided with a number of different inputs allowing the user to interface with the processor. In this illustrative embodiment, a microphone 29, an auxiliary input 25 (for input 33), a USB input 23, a GPS input 24 and a BLUETOOTH input 15 are all provided. An input selector 51 is also provided, to allow a user to swap between various inputs. Input to both the microphone and the auxiliary connector is converted from analog to digital by a converter 27 before being passed to the processor. Although not shown, numerous of the vehicle components and auxiliary components in communication with the VCS may use a vehicle network (such as, but not limited to, a CAN bus) to pass data to and from the VCS (or components thereof).

Outputs to the system can include, but are not limited to, a visual display 4 and a speaker 13 or stereo system output. The speaker is connected to an amplifier 11 and receives its signal from the processor 3 through a digital-to-analog converter 9. Output can also be made to a remote BLUETOOTH device such as PND 54 or a USB device such as vehicle navigation device 60 along the bi-directional data streams shown at 19 and 21 respectively.

In one illustrative embodiment, the system 1 uses the BLUETOOTH transceiver 15 to communicate 17 with a user's nomadic device 53 (e.g., cell phone, smart phone, PDA, or any other device having wireless remote network connectivity). The nomadic device can then be used to communicate 59 with a network 61 outside the vehicle 31 through, for example, communication 55 with a cellular tower 57. In some embodiments, tower 57 may be a WiFi access point.

Exemplary communication between the nomadic device and the BLUETOOTH transceiver is represented by signal 14.

Pairing a nomadic device 53 and the BLUETOOTH transceiver 15 can be instructed through a button 52 or similar input. Accordingly, the CPU is instructed that the onboard BLUETOOTH transceiver will be paired with a BLUETOOTH transceiver in a nomadic device.

Data may be communicated between CPU 3 and network 61 utilizing, for example, a data-plan, data over voice, or DTMF tones associated with nomadic device 53. Alternatively, it may be desirable to include an onboard modem 63 having antenna 18 in order to communicate 16 data between CPU 3 and network 61 over the voice band. The nomadic device 53 can then be used to communicate 59 with a network 61 outside the vehicle 31 through, for example, communication 55 with a cellular tower 57. In some embodiments, the modem 63 may establish communication 20 with the tower 57 for communicating with network 61. As a non-limiting example, modem 63 may be a USB cellular modem and communication 20 may be cellular communication.

In one illustrative embodiment, the processor is provided with an operating system including an API to communicate with modem application software. The modem application software may access an embedded module or firmware on the BLUETOOTH transceiver to complete wireless communication with a remote BLUETOOTH transceiver (such as that found in a nomadic device).

In another embodiment, nomadic device 53 includes a modem for voice band or broadband data communication. In the data-over-voice embodiment, a technique known as frequency division multiplexing may be implemented when the owner of the nomadic device can talk over the device while data is being transferred. At other times, when the owner is not using the device, the data transfer can use the whole bandwidth (300 Hz to 3.4 kHz in one example).

If the user has a data-plan associated with the nomadic device, it is possible that the data-plan allows for broad-band transmission and the system could use a much wider bandwidth (speeding up data transfer). In still another embodiment, nomadic device 53 is replaced with a cellular communication device (not shown) that is installed to vehicle 31. In yet another embodiment, the ND 53 may be a wireless local area network (LAN) device capable of communication over, for example (and without limitation), an 802.11g network (i.e., WiFi) or a WiMax network.

In one embodiment, incoming data can be passed through the nomadic device via a data-over-voice or data-plan, through the onboard BLUETOOTH transceiver and into the vehicle's internal processor 3. In the case of certain temporary data, for example, the data can be stored on the HDD or other storage media 7 until such time as the data is no longer needed.

Additional sources that may interface with the vehicle include a personal navigation device 54, having, for example, a USB connection 56 and/or an antenna 58, a vehicle navigation device 60 having a USB 62 or other connection, an onboard GPS device 24, or remote navigation system (not shown) having connectivity to network 61.

Further, the CPU could be in communication with a variety of other auxiliary devices 65. These devices can be connected through a wireless 67 or wired 69 connection. Auxiliary device 65 may include, but are not limited to, personal media players, wireless health devices, portable computers, and the like.

Also, or alternatively, the CPU could be connected to a vehicle based wireless router 73, using for example a WiFi 71 transceiver. This could allow the CPU to connect to remote networks in range of the local router 73.

Figure 2:
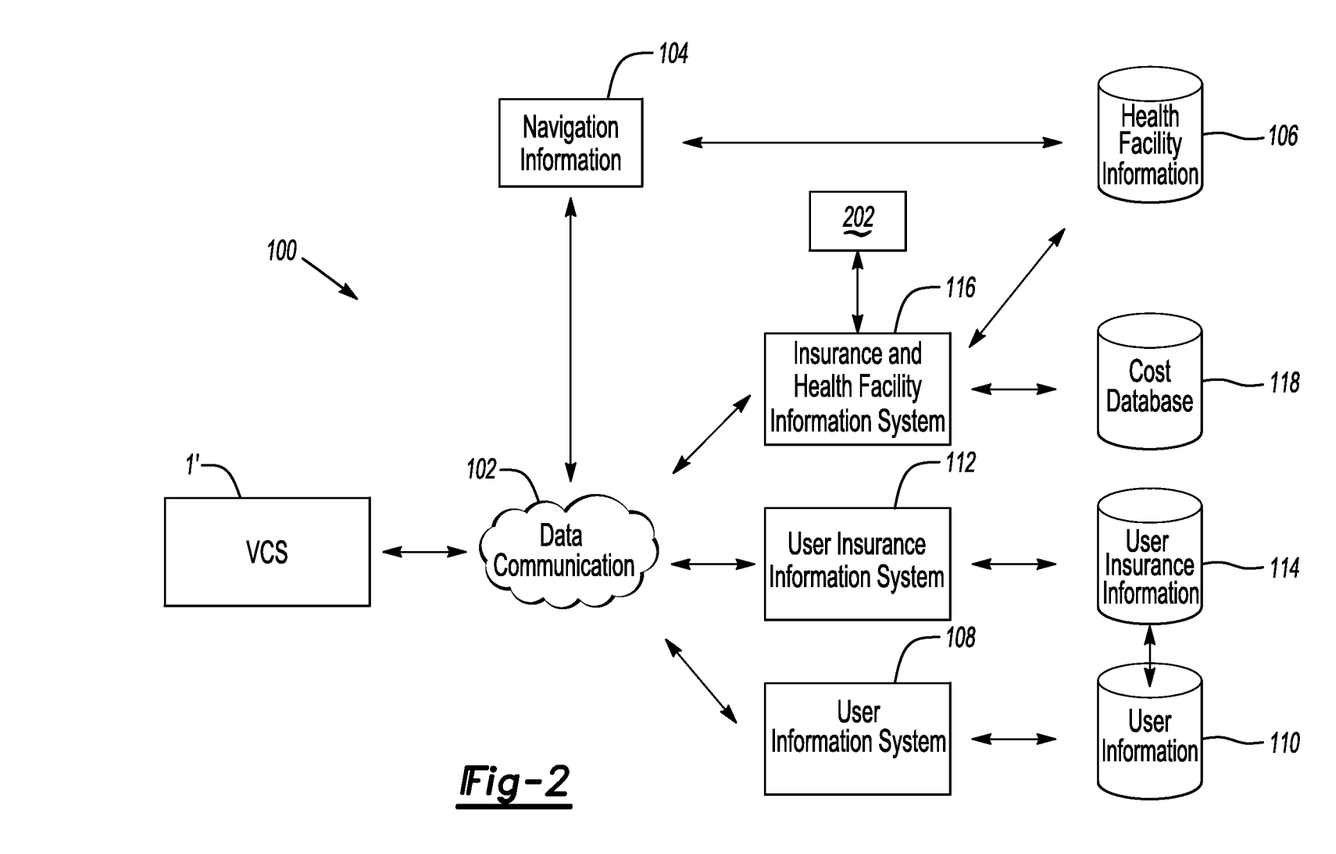
FIG. 2 is block diagram of a system that operates to provide health service cost information in a vehicle.
Figure 3:
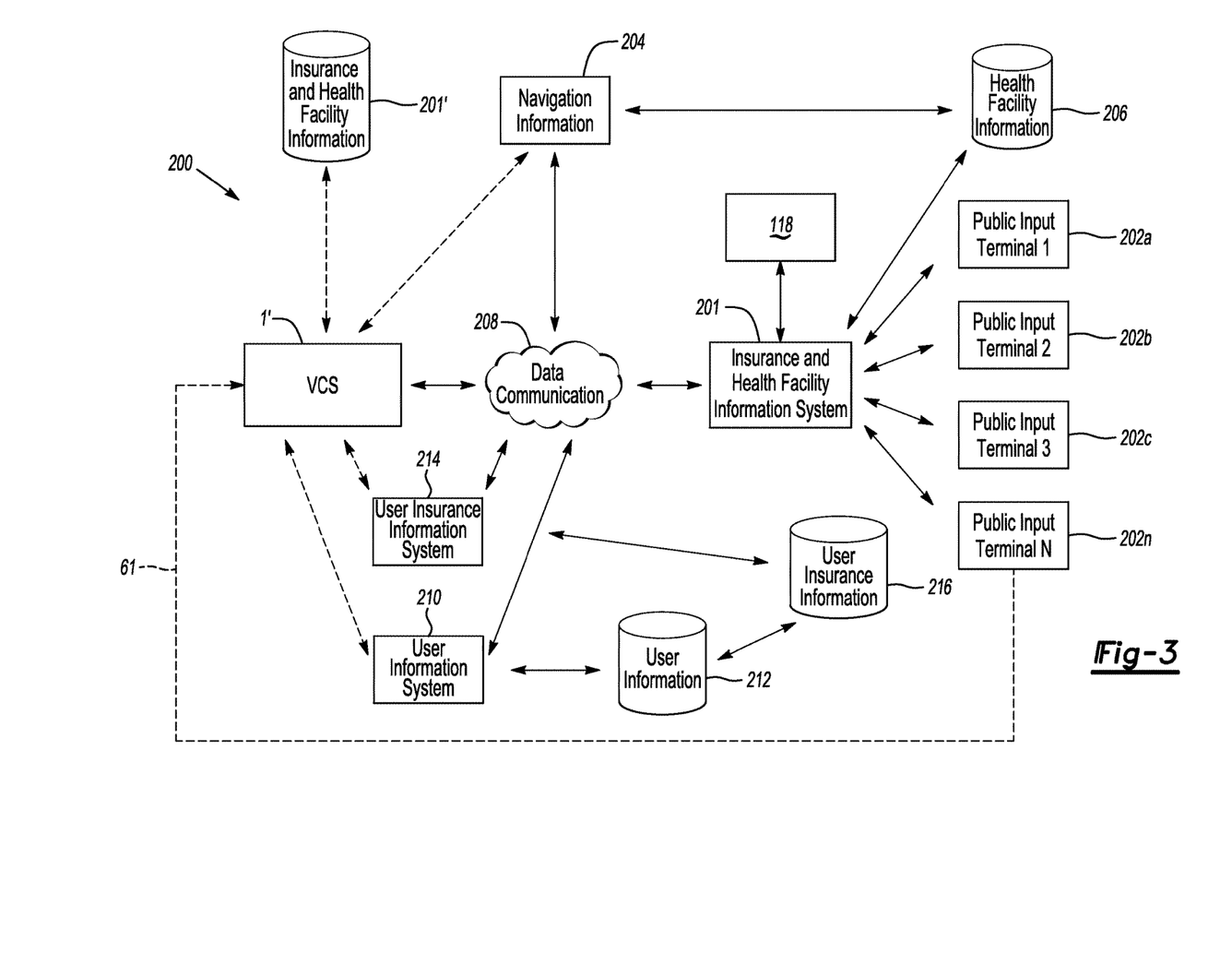
FIG. 3 is a block diagram of an additional or alternative system that operates to provide health facility and insurance cost information in a vehicle.

Health service cost information may be provided in the vehicle 31 from a multitude of different sources (individually or in combination). FIGS. 2 and 3 provide non-limiting examples of such sources. FIG. 2 is a block diagram of a system for providing health service cost information based on information collected by or from a health facility. FIG. 3 illustrates a block diagram of a system for providing health service cost information based on information obtain through public input. In some embodiments, such public input information may be known as "crowdsourced" information. The systems of FIGS. 2 and 3 may be individual systems or a combined system. While the various components are separately illustrated and described (in part for clarity), the system may be modified and re-arranged to best fit various implementations.

Referring first to FIG. 2, the VCS 1 (which corresponds to VCS 1 of FIG. 1) may be in data communication 102 with one or more subsystems. Data communication 102 may be an in-vehicle communication network (e.g., and without limitation, a vehicle network such as a CAN bus, GM-LAN, and the like) or network 61 (as illustrated in and described with respect to FIG. 1). In some embodiments, at least part of the system 100 may be remote from the vehicle such that VCS 1 may communicate data via network 61 and in-vehicle network 102.

The navigation information subsystem 104 may provide navigation data (including, but not limited to, map data and route data) to the VCS 1. Subsystem 104 may store 106 (e.g., in a database or on a computer-readable medium such as a DVD) geographic locations of health providers. In some embodiments, information about the health facilities may also be included. Such information may include information about one or more health facilities such as type of provider (e.g., hospital, dental clinic, urgent care, private practice, etc.), contact information, hours of service, services offered, and insurance plans accepted. When presented in the vehicle, these health providers may be presented along a travel route. In some embodiments, at least some of this health provider information may be stored at insurance and health facility information system 116, which will be described in further detail below.

User information subsystem 108 may provide information about the vehicle users (e.g., driver and/or passenger). The information may be stored as a user profile in storage medium 110 such as a database and/or memory. The user information may be provided by a vehicle user from a remote terminal (e.g., from a PC (not shown) or ND 53) and transmitted to the subsystem 108 via an Internet connection (e.g., using a member website such as www.syncmyride.com). Additionally or alternatively, the user information may be input and stored at the VCS 1. Additionally or alternatively, the user information may be input to and stored on a wellness device 67. User information may include identification information about the user (such as name, address, social security number, telephone number and the like). The user information may also include authentication information to authenticate (and identify) the user including, but not limited to, a vehicle identifier (such as a VIN), user identifier (such as a login using text, voice recognition, a key fob, or a combination of logins), mobile identifier (such as a MIN), or a combination of such identifiers. Additionally, user information may include health related information for a vehicle user (including, but not limited to, medical and dental) such as health history, health conditions, allergies, medications, and the like. The user profiles may be associated with the authentication information. The authentication identifier(s) may be transmitted from the vehicle 31 to user information system 108 for profile authentication and identification.

User insurance information subsystem 112 may provide information on the vehicle user's insurance plan including, but not limited to, type of plan, coverage, in-network providers, out-of-network providers, deductible, co-pays, co-insurance, insurance plan dependents, and other such information. Such information may be provided by a vehicle user, the vehicle user's employer, and/or an insurance company. The insurance information may be stored in a storage medium 114 (such as memory and/or a database) as insurance profiles associated with each vehicle user. In some embodiments, subsystem 112 may communicate with subsystem 108 for obtaining user information.

An insurance and health facility information subsystem 116 may provide health services cost information and health facility information. The information may be stored on a storage medium 118 including, but not limited to, memory and/or a database. In some embodiments, a vehicle user may download the cost information to a portable computer-readable medium (e.g., and without limitation, a DVD or flash drive) from a remote terminal for use in the vehicle 31. The health services cost information may be collected by or from a public or private health facility. In some embodiments, the information may be collected and maintained by the automotive OEM or a third-party partner of the OEM. The cost information may include the cost for one or more services at the health facility. The information may be organized based on service type (including surgical and non-surgical services) and the cost for each service. In some embodiments, the cost may be an average and/or estimated cost. Certainly, a service type is any health service offered by a health facility (including, but not limited to, general physicals, vaccinations, and the like). Further, health services may relate to any service in any human or non-human health related field.

Additionally, the subsystem 116 may include information about the health facility as described above.

In some embodiments, subsystem 116 may also be in communication with public user terminals 202. Further details will be described below.

FIG. 3 illustrates an additional or alternative system 200 for obtaining health service cost information in a vehicle. The information that is obtained may also include information about one or more health facilities such as information that is described above. In some embodiments, this information may be obtained from subsystem 204 (which may correspond to subsystem 104 in FIG. 2).

The VCS 1 (corresponding to VCS 1 of FIG. 1) may receive such information (for presentation to one or more vehicle users) from a network of public users 202a, 202b, 202c, 202n that provide input on health facility information and cost information. Public users 202 may be at one or more personal computers (PC) and/or a nomadic device (such as a mobile phone).

Figure 6:
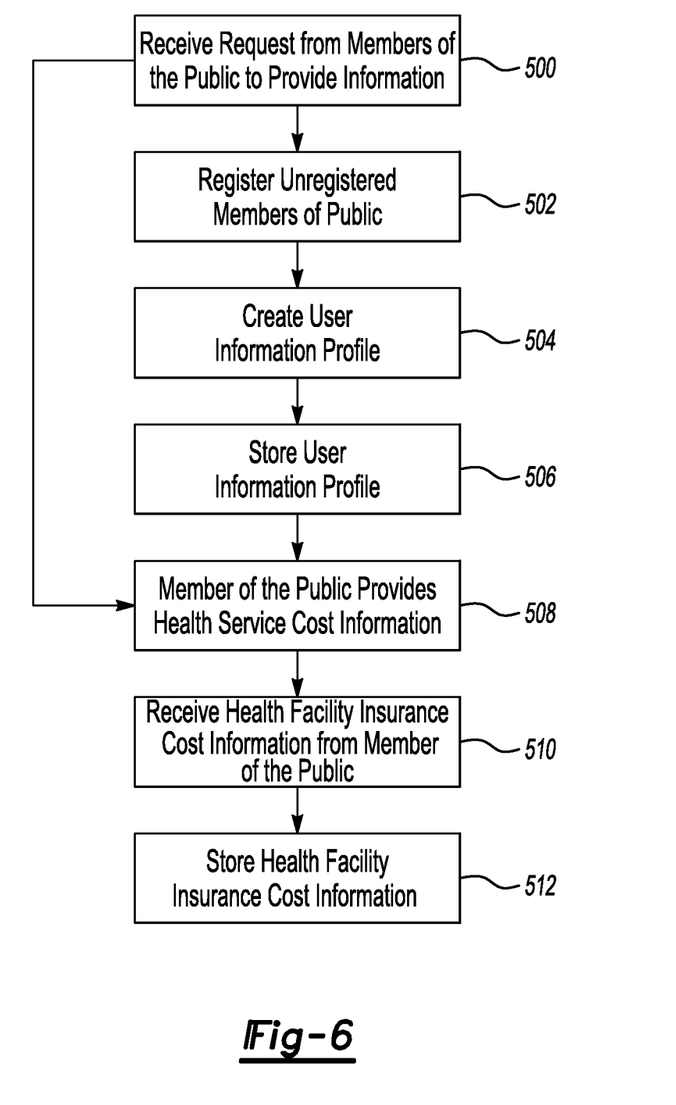
FIG. 6 is a block diagram of the process associated with obtaining publicly input health service information.

Referring to FIG. 6, a non-limiting process for creating the network of public users 202 is provided. A request may be received from a member of the public to be a public input user (block 500). A member of the public may be any person providing public input health service cost information. Such individuals may or may not register to become a member of the network of public input users 202. In some embodiments, such individuals may be required to register for system and member security purposes. Accordingly, in such embodiments, unregistered member may be registered (block 502).

A public input user may also be a member of a private network of public input users associated with an organization or business entity such as the automotive OEM or an insurance company. In such cases, the public input user may be registered by virtue of their association with the organization or business entity.

Registration for becoming a public input user may include creating a user profile (block 504). The user profile may include, but is not limited to, identification information for the public input user, login information, insurance provider information, insurance plan information, age, and gender. The user profile information may be stored in memory (e.g., at subsystem 201) (block 506).

If a public input user is already a contributor of health service cost information and/or health facility information or, if registration is required, a member of the network, step 500 may include receiving a request from such public input user to contribute information. Such a request may be identified by the user logging in (e.g., to a web-based application) or selecting an input command (e.g., a link or command button) on a graphical user interface. A non-limiting example of such an input command may be a link with a name or title requesting the public input user to contribute information.

The public input user may provide the contributing information (block 508). In addition to health service cost information and health facility information, such contributing information may include a rating/review of a health facility, a rating/review of insurance providers and plans, and a rating/review of health providers.

The contributing information may be received (block 510) and stored (block 512) at subsystem 201 (FIG. 3). The information may be received at the VCS 1 as described below.

Referring back to FIG. 3, the information from the public input user may be received by VCS 1 through insurance and health facility information system 201. System 201 may be an intermediary system which serves as an interface between public user 202 and the VCS 1. System 201 may store the health facility and insurance cost information provided by the public users 202 and provide the information to the VCS 1. The information may be stored in a storage medium (such as a database and/or memory). In some embodiments, the system 201 may be comprised of one or more terminals (such as servers) in data communication (not shown) with each other. For example, a terminal may serve as the interface for the public users 202 and comprise a user interface for interaction with and by the users 202. Another terminal may be the interface for the VCS 1 to obtain the public user 202 input.

In some embodiments, system 201 may also provide health facility information stored in database 206.

In some embodiments, system 201 may also be in communication with cost information database 118 so that such information (as described above) may additionally be provided at the VCS 1.

In some embodiments, as represented by the dashed lines, the insurance health facility information subsystem may be stored as memory (or another data storage medium) 201' on the VCS 1. Accordingly, information input by public users 202 may be stored 201' on the VCS 1. In this case, other than public user terminals 202, system 200 may be an in-vehicle system and data communication 208 may be an in-vehicle network. Public users 202 may communicate information to the VCS 1 over external network 61 (represented by the dashed line 61 in FIG. 3). Public users 202 may be given an identifier (such as a vehicle, user, and/or mobile identifier) in order to direct the public input to the intended vehicle user(s). The identifier(s) may be entered by the public user 202 as part of the public input message generation process.

System 201, user information subsystem 210, 212, user insurance information subsystem 214, 216 and navigation information subsystem 204, 206 may be counterpart subsystems to system 116, user information subsystem 108, 110, user insurance information subsystem 112, 114 and navigation information subsystem 104, 106 of FIG. 2. Details of these subsystems are described above. In some embodiments, subsystems 104, 108, 112 and 116 may be the same subsystem as subsystems 204, 210, 214 and 201 respectively.

Figure 4:
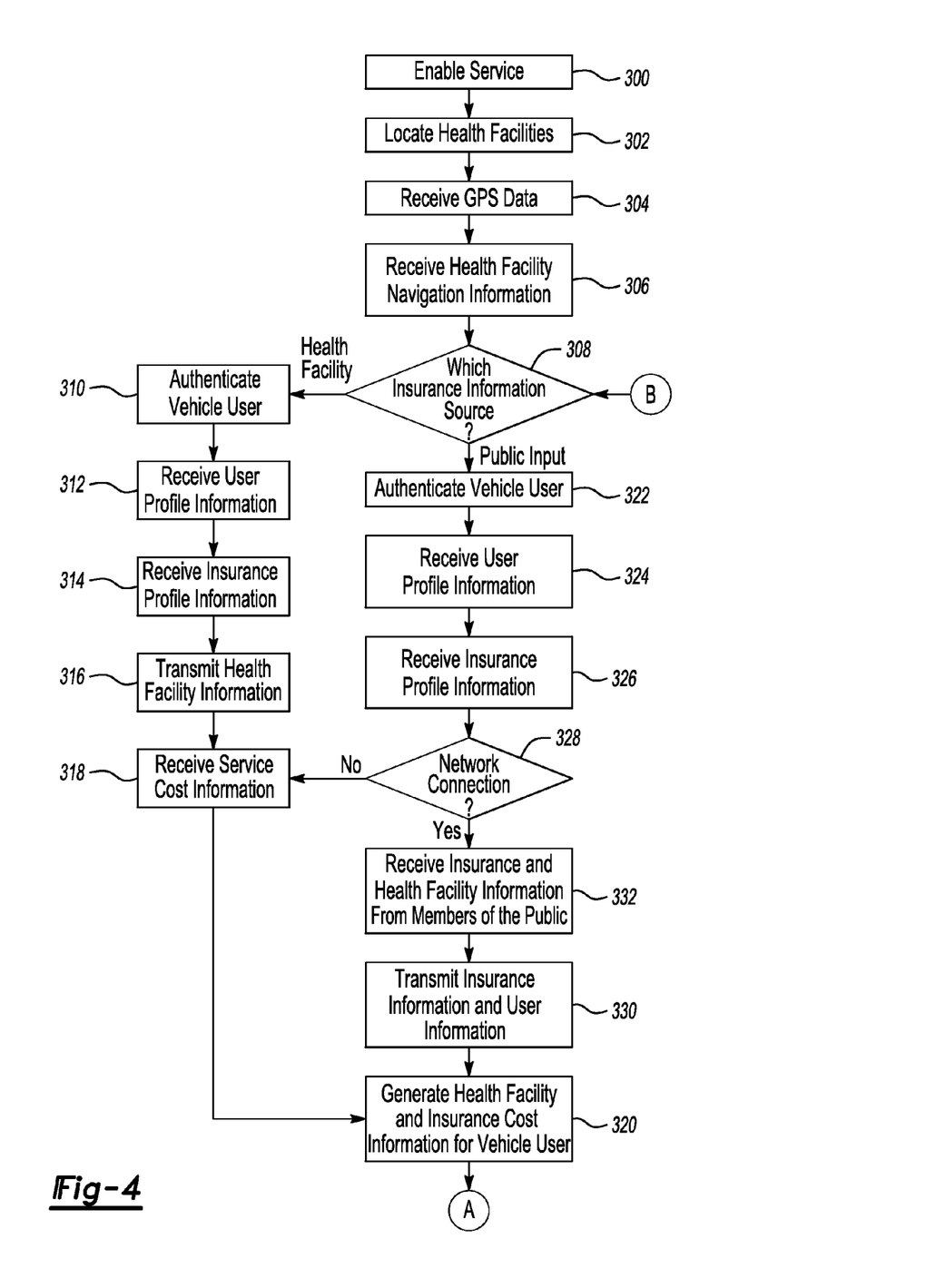
FIG. 4 is a block diagram of the process for providing health service cost information in a vehicle.

FIG. 4 illustrates the process for obtaining health service cost information in a vehicle. A software application may be downloaded or provisioned to the ND 53 or VCS 1 in order to provide this service in the vehicle. The download may occur at the factory, at the dealership, or after acquisition of the vehicle. The application may be downloaded using a network connection (such as, and without limitation, the Internet). Additionally or alternatively, the application may be downloaded to a computer-readable medium (e.g., and without limitation, a DVD, USB flash drive or memory stick) and loaded to the VCS 1 or ND 53 from the medium. Alternatively, the application may be provisioned directly (using a wired or wireless data connection) from a remote terminal to the VCS 1 or ND 53. In additional or alternative embodiments, the software application may run/execute on a computing system remote from the VCS 1 or ND 53 and be operated from the VCS 1 or ND 53 through a network (e.g., Internet) connection. In additional or alternative embodiments, the software may be programmed directly to the VCS 1.

Referring now to FIG. 4, the operation of providing health service cost information may be enabled (block 300). A vehicle user input such as a spoken (or other audible) command and/or a touch-based command (e.g., and without limitation, a button press) may be received at the VCS 1 instructing operation of the service to be enabled. Touch-based commands may be received from such non-limiting, non-exhaustive input controls as the vehicle steering wheel, center stack, and/or a touchscreen display.

Instructions may be received at the VCS 1 to locate health facilities (block 302) in response to enabling operation. Such instructions may be transmitted automatically. In some embodiments, such instructions may be the input from a vehicle user for enabling operation of this service. As a non-limiting example, the user may press a button that causes a health facility search to be performed and/or say "locate health facilities." In some embodiments, health facilities may be located in response to input from the wellness device 67 monitoring the health of the vehicle user.

In some embodiments, based on the input from the wellness device 67, the type of service needed by the vehicle user may be determined. As a non-limiting example, if the wellness device 67 detects an irregular heartbeat, this information may be used to locate health facilities with an EKG. The type of health service needed or desired by the vehicle user may additionally or alternatively be provided by the vehicle user or other vehicle occupant. As a non-limiting example, a menu of services offered by the identified health facilities may be displayed on display 4 for selection. Additionally or alternatively, the services needed or desired may be verbally and/or textually input using predefined commands or free-form or natural language commands. In any case, the health condition event may be an emergency or non-emergency.

To locate health facilities, GPS data may be received to determine the location of the vehicle 31 (block 304). At subsystem 104, 204, using GPS data and/or location information (e.g., and without limitation, an address) of the vehicle, health facility, or both, health facility navigation information may be received at the VCS 1 (block 306). The health facility navigation information may include, but is not limited to, map data and route data based on the location of the vehicle and/or health facilities, and health facilities within a geographic radius of, or distance from, the vehicle 31. The navigation information may include additional information as described above. In some embodiments, the health facility navigation information may include health facilities along a travel route. In this case, destination information may additionally be used to locate health facilities.

A vehicle user may receive health service cost information from one or more information sources. Accordingly, the vehicle user may be instructed/requested by the VCS 1 to select an information source from which to receive the information (block 308). Alternatively, the vehicle user may preselect an information source (for example, during application setup and/or profile registration). The preselection may be stored in memory (e.g., at the VCS, on the ND 53, or at a remote terminal) for access by the software. Two non-limiting, non-exclusive examples of such information sources include health service cost information by or from a health facility and public input health service cost information. As will be described with respect to FIG. 5, a vehicle user may also receive and be presented with health service cost information from multiple information sources. The information may be presented together or separately.

For clarity, system 100 will be used to describe the operation with respect to the health facility information source and system 200 with respect to the public input information source. However, as described above, system 100 and 200 may be a single system.

Using health facility information, the user information may be received (block 312) from the user information subsystem 108. The user insurance information may also be received (block 314) from the user insurance information subsystem 112. The user authentication information may be transmitted to the subsystem 108 or 112 in order to receive the user information and the user insurance information (block 310). In some embodiments, the user authentication information may be transmitted when enabling operation of the service. As such, the user may already be authenticated. In alternative embodiments, authentication may occur at multiple times (e.g., when enabling operation and receiving user information and user insurance information).

Health facility information may be transmitted to obtain the health facility and service cost information for the identified health facilities (block 316). The health facility information may be information obtained from the health facility navigation information (e.g., and without limitation, GPS information, location information, or other identification information such as a name). Using the health facility information, the health service cost information for the health facilities may be received from subsystem 116 (block 318).

Some or all of the received information (e.g., the user information, insurance information, and service cost information) may be used to generate the health facility service cost information (block 320). The service cost information may include the portion of the service that may be covered based on the user's insurance plan (obtained from the user insurance information). This may be expressed as a percentage and/or a monetary amount. Additionally or alternatively, the cost information may include a monetary amount owed by the vehicle user. The monetary amount may include the cost of the service(s) and/or incidental/associated costs for the service including, but not limited to, co-pays, co-insurance, deductibles, and the like. The monetary amount may be calculated from the information obtained from the user insurance information and the health facility cost information. The monetary amount may be presented (as described with respect to FIG. 5) as a total or as itemized values. Further details of determining the health service cost information are described with respect to FIG. 8.

In some embodiments, the vehicle user's service cost may be calculated as falling within a range of cost values. This range may be calculated as a percentage or monetary value.

Referring back to block 308, another source for cost information may be cost information obtained from public input. As described above, the vehicle user may be authenticated (block 322), user information may be received (block 324), and the user insurance information may be received (block 326).

The public user input 202 may be received from systems capable of communicating with the VCS 1 over a network connection (e.g., the Internet or a LAN). Accordingly, it may be determine if a network connection is available (block 328). If not, the operation may be suspended and/or the vehicle user may be notified that a network connection is not available. In some embodiments, as shown in FIG. 4, if no connection is available, the health facility provided cost information may be received (as described above) instead.

If a network connection is available, the user information and/or user insurance information may be transmitted to the system 201 (block 330). The user information and/or user insurance information may be used to determine if the vehicle user's personal information and/or insurance information correspond to information for one or more public input users 202. Accordingly, the vehicle user may be provided service cost information from the public input that is most relevant and applicable to the vehicle user. Further details of this operation will be described with respect to FIG. 7.

The public input information may include the cost for the public input user for the service performed. The cost may include, but is not limited to, costs for the service such as, and without limitation, the amount covered by insurance (as a percentage and/or monetary amount) and/or the monetary amount owed by the public input user. The monetary amount owed may also include incidental/associated cost such as, and without limitation, co-payment, co-insurance, deductibles, and the like. The cost information may be provided by the public input user based on information received from the public input user's insurance provider (such as an explanation of benefits (EOB)) and/or recent payment information. The information from the public input user may also include, but is not limited to, identification information for the health facility, information about the health facility where the health service was completed, the insurance plan owned by the public input user, the insurance provider for the public input user, and the public input user's age and/or gender. The information from the public input user may be presented to the vehicle user as described below with respect to FIG. 5.

The public input user information may be received from subsystem 201 (block 332) and used to generate health service cost information for the vehicle user (block 320). The health service cost information may also include information about the health facility. Further details of determining the health service cost information are described with respect to FIG. 7.

Figure 5:
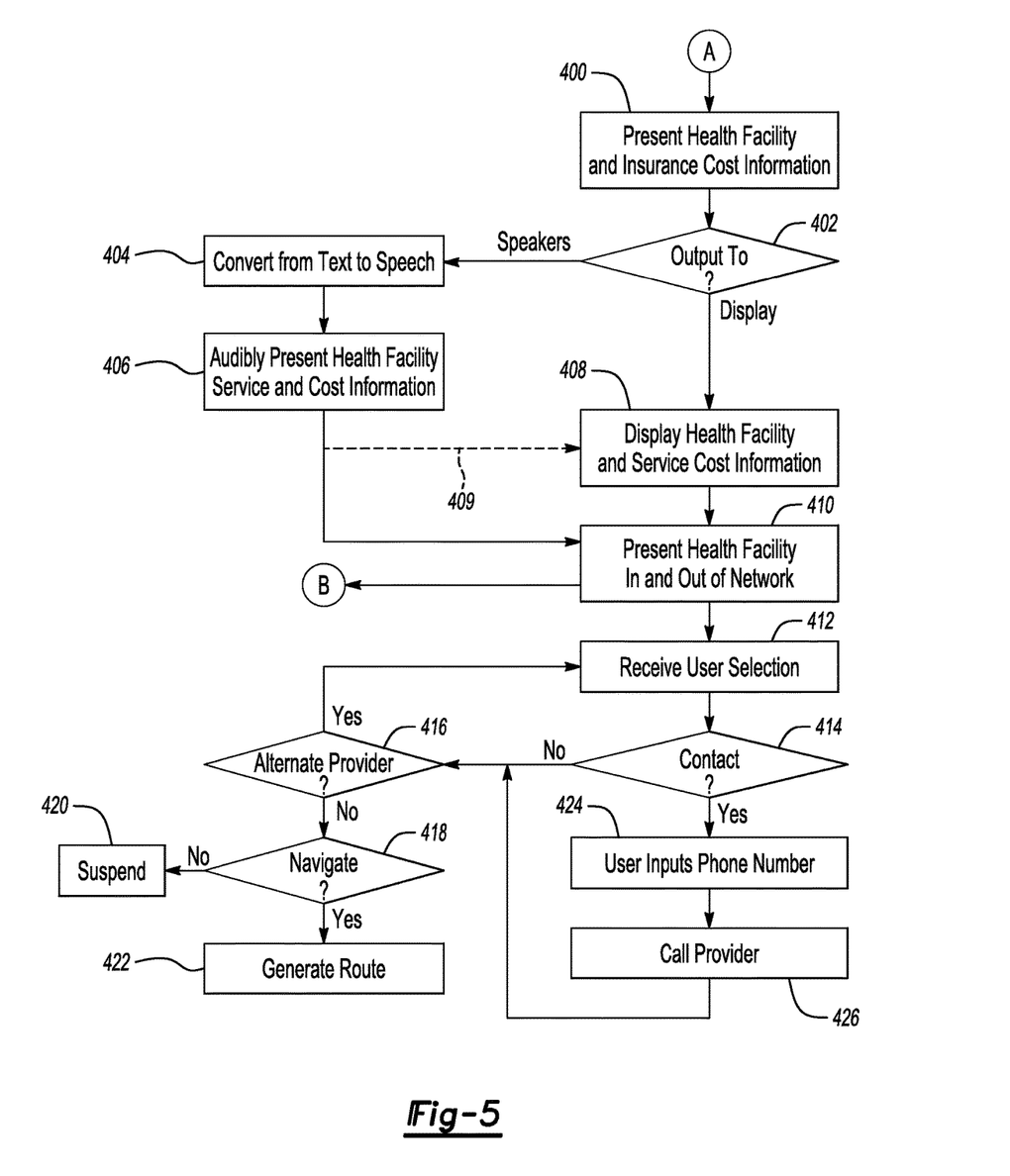
FIG. 5 illustrates further operation associated with providing health facilities and service cost information in a vehicle.

FIG. 5 illustrates further operation (as represented by circle block A) of the health service cost information determination process for a vehicle user.

As represented by block 400, the generated health service cost information may be presented in the vehicle. The information may be presented audibly (e.g., via speakers 13) and/or visually (e.g., on display 4) (block 402).

In order to present the information from the speakers, the information may be converted from text to speech (block 404). This conversion may occur at the VCS 1 (using installed text-to-speech software), on the ND 53, or at a remote computing system operable to communicate with VCS 1 via network connection 61. The cost information, once converted to speech, may be presented in audible form from speakers 13 (block 406).

The service cost information and health facility information may be displayed on display 4 (block 408). In some embodiments, the information may be presented audibly and visually (as represented by dashed line 409).

Based on the vehicle user's insurance plan, health facilities that are "in-network" and "out of network" may be identified when the service cost information is determined. Accordingly, the identified health facilities may be presented in the vehicle (audibly and/or visually) as in-network or out-of-network (block 410). In some embodiments, when the information is displayed, the presentation may include identifiers representing a health facility as in-network or out-of-network. Such identifiers may include graphics (such as icons), colors, or both.

As described above, the vehicle user may obtain service cost information from multiple information sources. In this case, as represented by circle block B in FIGS. 4 and 5, a determination may be made which other information source has been selected by the vehicle user. Based on the selection, the operation may be performed as described above.

Alternatively, the user may select a health facility to visit based on the health facility and service cost information presented (block 412). When selected, the user may be given an opportunity to contact the health service provider (block 414). If the vehicle user does not contact the provider, it may be determined, based on user input at the VCS 1, if an alternate health service provider is selected by the vehicle user (block 416). If an alternate provider is not selected, it may be determined, based on user input at the VCS 1, if the user desires to be navigated to the health service provider (block 418). If not, the operation may be suspended (block 420). In some embodiments, the operation may be suspended after a period of inaction by the vehicle user. Otherwise, the route may be generated to the health facility (block 422).

If the user does contact the health service provider based on user input at the VCS 1 (block 424), a call may be placed to the provider (block 426). The vehicle user input may be a spoken command to call or a selection of a link tied to the phone number for the service provider.

In some cases, after contacting (or attempting to contact) a provider, the vehicle user may choose an alternate provider (block 416). This may be identified by, for example, user input at the VCS 1 (e.g., an input command for alternate providers). As one example, the provider may be unreachable. Alternatively or additionally, the provider may not have appointment availability. Such examples are provided for explanation and not intended to be limiting. Accordingly, there may be additional reasons that the vehicle user chooses an alternate provider. The operation associated with selecting an alternate provider is described above.

Figure 7:
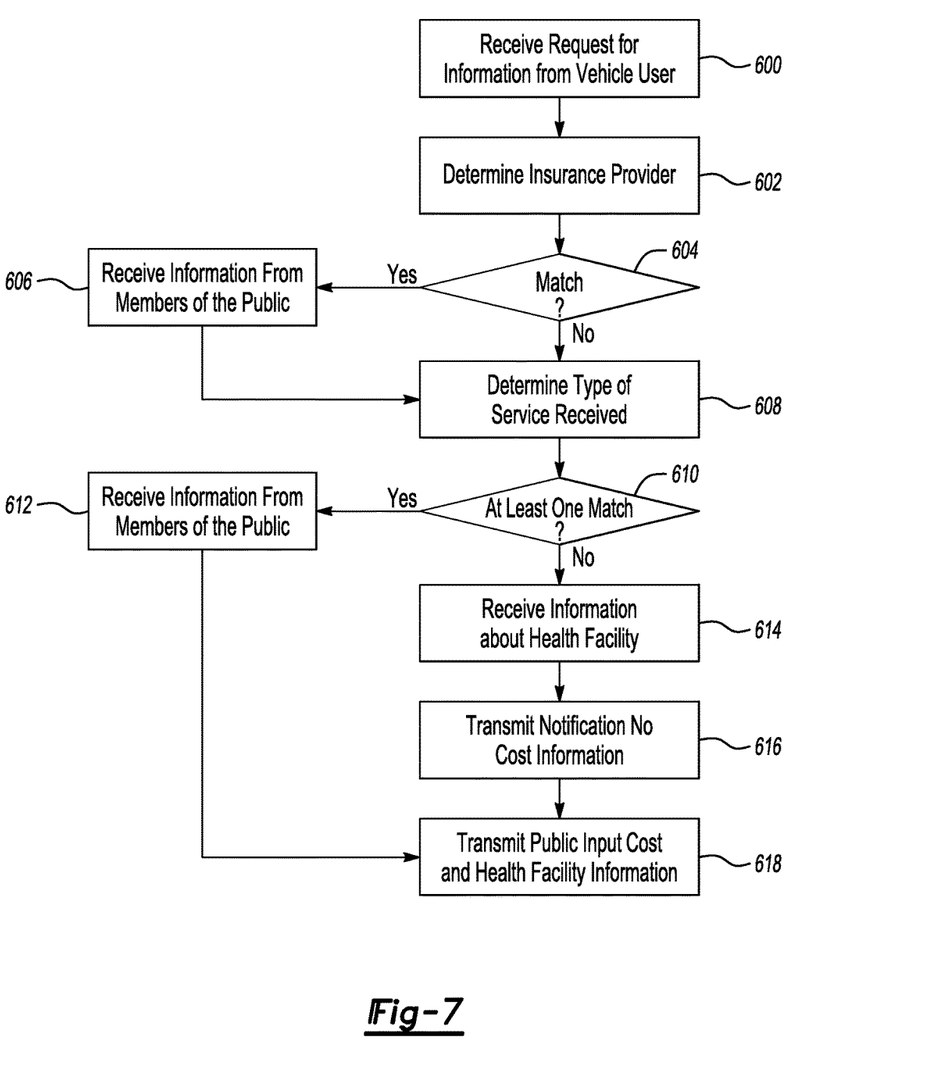
FIG. 7 illustrates a process for obtaining health service costs for a vehicle user based on publicly input health service information.

FIG. 7 shows the process for determining the public input health facility cost information to present in the vehicle 31. The request for public input health service and health facility information may be received at the subsystem 201 (block 600). The transmitted vehicle user information and insurance information (block 330) received at the subsystem 201 may be included in the request. From the insurance profile information, the vehicle user insurance provider may be determined (block 602).

As described above, information from the public input users may be compared to the vehicle user information so that the vehicle user is provided relevant and applicable public input information. Accordingly, it may be determined if there is a match between insurance providers of the vehicle users and any one or more public input users (block 604). If so, the public input users having the same or similar insurance plan and/or provider as the vehicle user may be identified. Based on the match, the public input information by these public input users may be received (block 606). In addition, the type of service for the public input user may be determined (block 608). Alternatively, the type of service may be determined if there is no match between the insurance plan/providers.

An additional match determination (block 610) may be performed to determine if there is at least one match for either or both the insurance information or the service type provided by the member(s) of the public. If there is at least one match, the matching public input users may be identified and the information provided by these public input users may be received (block 612). The public input information may be transmitted for presentation at the VCS 1 (block 618).

If there is no match of service types and insurance providers/plans, general information about the health facility may be received (block 614). This may include, but is not limited to, rating/reviews, contact information, hours of operation, and other general information. A notification may be generated that no health service cost information is available based on the service type and the insurance plan/provider information (block 616). The notification and the health facility information may be transmitted for presentation to the vehicle user (block 618).

It will be appreciated that the operation of FIG. 7 may occur serially or in parallel. Further, the order of the steps in FIG. 7 is non-limiting such that it may be re-arranged without departing from the scope of the invention.

Figure 8:
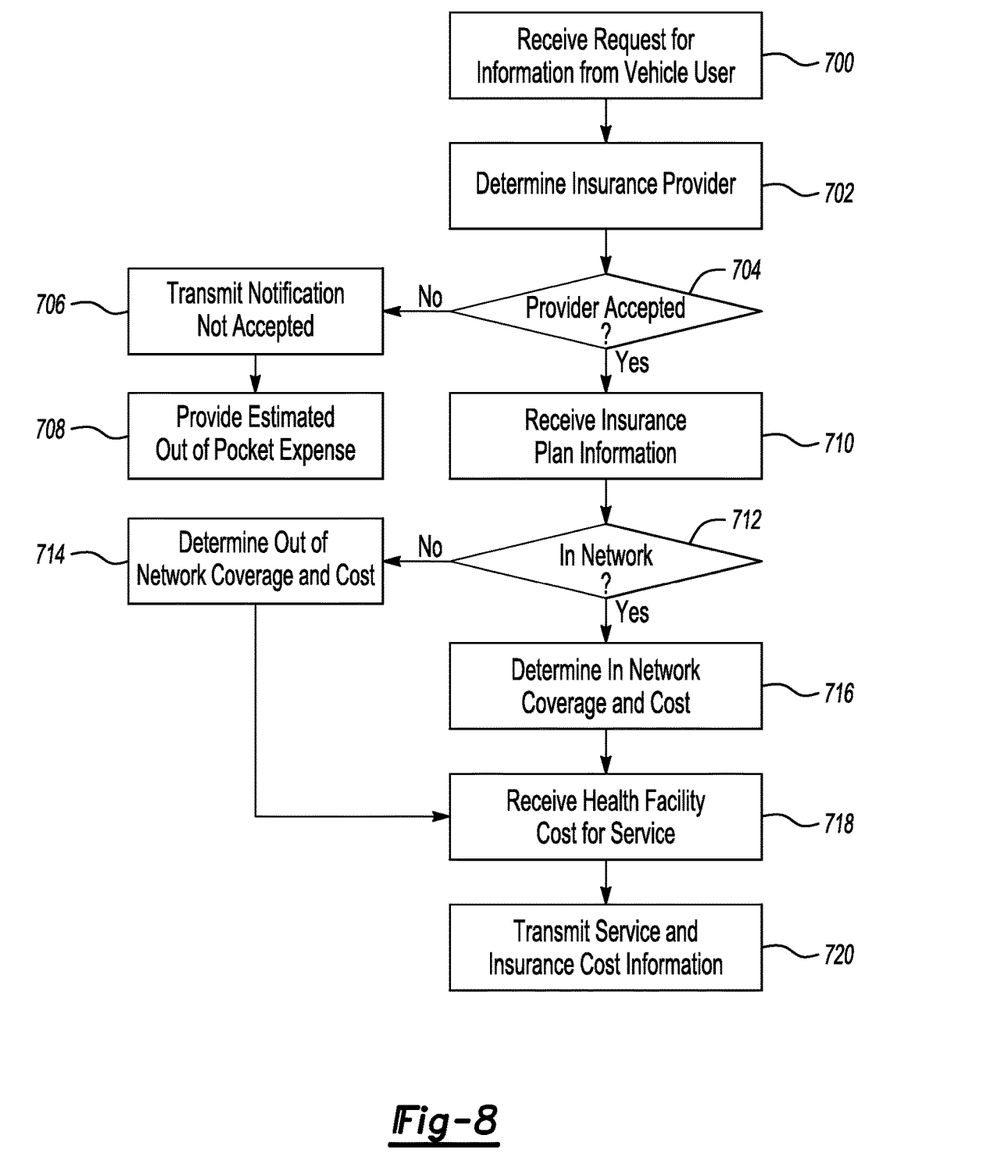
FIG. 8 illustrates a process for obtaining health service costs for a vehicle user based on health service cost information from a health facility.

FIG. 8 shows the process for determining the health service cost information provided by a health facility to present in the vehicle 31. The request for health service cost information may be received at the subsystem 116 (block 700). The transmitted health facility information (block 316, FIG. 4) received at the subsystem 116 may be included in the request. From the user insurance profile information 112, the insurance provider and/or plan may be determined (block 702).

It may be determined if the insurance provider is accepted at the identified health facility (block 704). If not, a notification may be generated that the provider is not accepted (block 706). Additionally, the estimated out of pocket expenses for the vehicle user may be determined (block 708).

Otherwise, if the provider is accepted, the insurance plan information may be received (block 710). From the plan information, it may be determined if the health facility is in-network or out-of-network (block 712). If the health provider is out-of-network, the coverage for the out-of-network provider may be determined based on the vehicle user's plan (block 714). If the provider is in-network, however, the in-network coverage may be determined (block 716).

The health service cost information may be determined using the information gathered from the vehicle provider's insurance plan (block 718). The health service cost information may be transmitted for presentation in the vehicle (block 720).

In some embodiments, the health service cost information may be calculated at the ND 53 and/or VCS 1. Additionally or alternatively, the health service cost information may be calculated at a remote computing system in network communication with the VCS 1.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A computer-implemented method comprising:
receiving a vehicle geographic location;
identifying, at a receiving computer, a health facility based on the geographic location;
receiving vehicle user health condition information and health insurance information;
determining, at the receiving computer, a health care service cost for the vehicle user at the identified health care facility based on the vehicle user's health condition and health insurance information;
presenting the health care service cost within the vehicle;
receiving selection of a health facility; and
placing a call, through a wireless device connected to a vehicle computer, to the selected health facility.

2. The computer-implemented method of claim 1 wherein presenting the health care service cost includes presenting the cost audibly, visually, or both.

3. The computer-implemented method of claim 1 further comprising:
Monitoring, at the vehicle computer, the health condition of the vehicle user in the vehicle;
receiving at the receiving computer the health condition based on the monitoring.

4. The computer-implemented method of claim 1 wherein the receiving computer is remote from the vehicle, the method further comprising communicating at the vehicle computer with the receiving computer over a data network connection.

5. The computer-implemented method of claim 4 wherein the receiving computer is included in a network of one or more members of the public.

6. The computer-implemented method of claim 5 wherein determining the health care service cost is based on information from the network.

7. The computer-implemented method of claim 1 further comprising:
generating a route to the selected health facility; and
navigating to the health facility based on the route.

8. A system for providing health care facility information in a vehicle, the system comprising:
at least one computer configured to receive information from one or more members of the public including health care service costs and health care insurance information for the one or more members of the public; and
at least one vehicle computer housed in a vehicle communicating with the at least one computer configured to:
receive health care insurance information for a vehicle user;
receive a health care service cost from the at least one computer based on the information from the one or more members of the public, wherein the information is applicable to the vehicle user based on the health care insurance information for the vehicle user and the health care insurance information for the one or more members of the public;
present the health care service cost;
receive selection of a health facility; and
place a call, through a wireless device connected to a vehicle computer, to the selected health facility.

9. The system of claim 8 wherein the at least one vehicle computer is further configured to store the information from the one or more members of the public.

10. The system of claim 8 wherein the at least one vehicle computer is further configured to determine if the information from the one or more members of the public is applicable to the vehicle user based on a service type for the vehicle user and a service type for the one or more members of the public.

11. The system of claim 8 wherein the at least one vehicle computer is further configured to:
receive health condition information for a vehicle user; and
receive the health care service cost further based on the health condition information.

12. The system of claim 11 further comprising a wellness device communicating with the at least one vehicle computer and configured to receive the health condition information.

13. The system of claim 8 further comprising memory storing health care service cost obtained from a health care facility.

14. The system of claim 13 wherein the memory is on at least one computer remote from the vehicle.

15. The system of claim 13 wherein the communicating is over the Internet, wherein the at least one vehicle computer is further configured to:

determine if an Internet connection is available; and
if not, receive the health care service cost from memory storing the health care cost.

16. A system comprising:
a processor configured to:
receive information identifying a health-service cost information source;
transmit user insurance information to obtain health-service cost information;
receive the health-service cost information from the identified source;
present the health-service cost information at a vehicle computer;
receive selection of a health facility offering a health-service in accordance with the received cost; and
placing a call, through a wireless device connected to the vehicle computer, to the selected health facility.

17. The system of claim 16 wherein the source is cost information obtained from a health facility.

18. The system of claim 16 wherein the source is cost information from one or more members of the public.

19. The system of claim 16 wherein the processor is further configured to:
receive information identifying one or more health facilities; and
determine, based on the vehicle user insurance information, if the one or more health facilities are a member of an insurance network; and
if so, present the member health facilities.

20. The system of claim 19 wherein the processor is further configured to present the member and non-member health facilities.

21. The system of claim 16 wherein the processor is further configured:
receive information about one or more health facilities; and
present the health facility cost information and the information about the one or more health facilities.

22. The system of claim 21 wherein the information about the one or more health facilities includes at least one of type of provider, contact information, hours of service, services offered, and insurance plans accepted.

* * * * *